US010618522B2

(12) United States Patent
Liu et al.

(10) Patent No.: US 10,618,522 B2
(45) Date of Patent: Apr. 14, 2020

(54) DROWSINESS DETECTION AND INTERVENTION SYSTEM AND METHOD

(71) Applicant: Hong Kong Productivity Council (HKPC), Hong Kong (HK)

(72) Inventors: Yin Bo Liu, Hong Kong (HK); Chi Hang Louie, Hong Kong (HK); Man Kit Bryan So, Hong Kong (HK); Tin Yan Chan, Hong Kong (HK); Wu Ming Lai, Hong Kong (HK); Ka Yin Leung, Hong Kong (HK); Yuk Sum Wong, Hong Kong (HK)

(73) Assignee: Hong Kong Productivity Council (HKPC), Hong Kong (CN)

( * ) Notice: Subject to any disclaimer, the term of this patent is extended or adjusted under 35 U.S.C. 154(b) by 0 days.

(21) Appl. No.: 16/361,331

(22) Filed: Mar. 22, 2019

(65) Prior Publication Data
US 2019/0299999 A1  Oct. 3, 2019

Related U.S. Application Data

(60) Provisional application No. 62/648,422, filed on Mar. 27, 2018.

(30) Foreign Application Priority Data

Sep. 27, 2018  (CN) .......................... 2018 1 1133826
Sep. 27, 2018  (CN) ....................... 2018 2 1584138 U

(51) Int. Cl.
*B60W 40/08* (2012.01)
*B60W 50/14* (2020.01)
(Continued)

(52) U.S. Cl.
CPC ........... *B60W 40/08* (2013.01); *A61B 5/0402* (2013.01); *A61B 5/0816* (2013.01); *B60W 50/14* (2013.01);
(Continued)

(58) Field of Classification Search
CPC ................ B60W 40/08; B60W 50/14; B60W 2040/0872; B60W 2040/0827;
(Continued)

(56) References Cited

U.S. PATENT DOCUMENTS 10,136,853 B2 * 11/2018 Heinrich .............. A61B 5/0064
10,390,762 B2 *  8/2019 Romesburg ........ A61B 5/14551
(Continued)

OTHER PUBLICATIONS

Zhengbo Zhang, et al., "Adaptive motion artefact reduction in respiration and ECG signals for wearable healthcare monitoring systems", Medical & biological engineering & computing, 52:1019-1030, 2014.
(Continued)

*Primary Examiner* — Fekadeselassie Girma
(74) *Attorney, Agent, or Firm* — Spruson & Ferguson (Hong Kong) Limited

(57) ABSTRACT

An in-vehicle monitoring and intervention system for detecting whether a driver in a vehicle is drowsy by monitoring a plurality of physiological signals of the driver is provided. The in-vehicle monitoring and intervention system includes at least a processor and an apparatus, the apparatus can be integrated into a seat belt or attached thereto as a discrete hardware apparatus, which includes at least an ECG sensor, a respiratory sensor, an acceleration sensor, a filtering system, and an intervention module. The filtering system further comprises one or more filters for suppressing noise and reducing motion artifacts. The processor is configured to compare the detected physiological signals with the signals stored in a learning module of the in-vehicle monitoring and intervention system for determining the drowsiness state. If the driver is determined to be drowsy, a warning signal is outputted to alert the driver.

18 Claims, 9 Drawing Sheets

(51) Int. Cl.
*G06K 9/00* (2006.01)
*A61B 5/08* (2006.01)
*A61B 5/0402* (2006.01)

(52) U.S. Cl.
CPC . *G06K 9/00845* (2013.01); *B60W 2040/0827* (2013.01); *B60W 2040/0872* (2013.01); *B60W 2050/143* (2013.01)

(58) Field of Classification Search
CPC ........... B60W 2050/143; A61B 5/0402; A61B 5/0816; A61B 5/0205; A61B 5/7207; A61B 5/0245; A61B 5/024; A61B 5/02405; A61B 5/725; A61B 5/7267; A61B 5/168; A61B 5/18; G06K 9/00845
See application file for complete search history.

(56) References Cited

U.S. PATENT DOCUMENTS

| | | | |
|---|---|---|---|
| 2011/0021928 A1* | 1/2011 | Giovangrandi | G16H 50/20 600/484 |
| 2011/0137188 A1* | 6/2011 | Kuo | A61B 5/0245 600/509 |
| 2011/0137189 A1* | 6/2011 | Kuo | A61B 5/0245 600/509 |
| 2011/0201904 A1* | 8/2011 | Cusimano Reaston | A61B 5/00 600/301 |
| 2011/0224565 A1* | 9/2011 | Ong | A61B 5/4824 600/509 |
| 2015/0223759 A1* | 8/2015 | Ong | A61B 5/01 600/301 |
| 2016/0196635 A1* | 7/2016 | Cho | G06T 3/40 345/660 |
| 2016/0270720 A1* | 9/2016 | Luo | A61F 5/56 |
| 2018/0229674 A1* | 8/2018 | Heinrich | B60R 16/0231 |
| 2019/0000394 A1* | 1/2019 | Chen | A61B 5/6843 |
| 2019/0357834 A1* | 11/2019 | Aarts | A61B 5/18 |

OTHER PUBLICATIONS

Zoran Fejzo et al., "Adaptive Laguerre-lattice Filters", IEEE Transactions on Signal Processing, vol. 45, No. 12, Dec. 1997.

* cited by examiner

DROWSINESS DETECTION AND INTERVENTION SYSTEM AND METHOD

CROSS-REFERENCE TO RELATED APPLICATIONS

This application claims the benefit of U.S. Provisional Patent Application No. 62/648,422, filed on Mar. 27, 2018, China Utility Model Patent Application No. 201821584138.0, filed on Sep. 27, 2018, and China Invention Patent Application No. 201811133826.X, filed on Sep. 27, 2018, which are incorporated by reference herein in its entirety.

FIELD OF THE INVENTION

The present disclosure generally relates to an in-vehicle monitoring and intervention system, and more particularly relates to a system and a method with adaptive motion artifact cancellation for detecting the physiological signals of a driver using a seat belt, determining the drowsiness condition and performing an intervention.

BACKGROUND OF THE INVENTION

The design and manufacture of vehicles are mature with well-established guidelines and standards to ensure the safety and flawlessness of the vehicles. However, the sleepiness or fatigue condition of the drivers is causing so many accidents and casualties that cannot be avoided by the toughness of the vehicles. In order to prevent the occurrence of vehicular accidents, more preemptive measures are required for achieving early detection of inattentive or drowsy driving.

According to the "Sleep in America" poll conducted by National Sleep Foundation (NSF), there were around 60% adult drivers admitted that they had driven a vehicle while feeling drowsy in the past year, which could be representing as many as 168 million drivers in the US. In 2014, the National Highway Traffic Safety Administration (NHTSA) had identified 846 fatalities that were drowsy driving related. This can be caused by the fatigue of the driver, the influences of drugs or alcohol, and other unexpected medical conditions, e.g., heart attack, stroke, etc. These dangerous situations are some of the major causes of road accidents in the US and other countries as well, posing significant risk and danger to the driver, other passengers, occupants of nearby vehicles and pedestrians.

In view of the issues raised above, various monitoring measures have hitherto been used or proposed to determine the attentiveness of the driver. Conventional methods use "steering pattern" and "steering torque" to analyze the mental state of the driver by detecting the steering pattern and lane-keeping behavior. However, the geometric characteristics of the road, weather conditions and road conditions may affect the steering angle and reduce the accuracy of the system. Another method is an image-based approach which captures the head pose, facial expression or eyes movement of the driver for determining whether the driver is awake or drowsy. However, the accuracy may also be affected by artifacts such as sunglasses or expressionless of the driver.

In some other applications, heartbeat sensors are embedded in the car seat to measure a driver's stress level. Typically, the car seat would monitor a driver's heartbeat through a plurality of sensors on the surface of the backrest that detect electrical impulses from the heart. Such a system has the intention to monitor the heart rate and alert when the driver may fall asleep at the wheel. However, embedding the sensors in the car seat increases the complication when installing and repairing. In most cases, such a system can only be integrated when manufacturing the car, and cannot be added to an existing car. The flexibility of the system is also limited and may not fit perfectly on all types of vehicles.

Accordingly, there is a need in the art for an in-vehicle monitoring and intervention system which overcomes the drawbacks of the prior art systems, provides accurate measurement of the drowsiness condition of a driver, and responds quickly to perform an intervention and alert the driver when the driver is in a drowsy state.

SUMMARY OF THE INVENTION

An exemplary embodiment of the present disclosure provides a method and an in-vehicle monitoring and intervention system determining a drowsiness state of a driver in a vehicle. The method includes a detection process that can comprise measuring electrocardiogram (ECG) signals, respiratory signals and acceleration signals; a filtering process for performing noise suppression and adaptive motion artifact cancellation; and a determination process for extracting one or more heart rate variability (HRV) parameters from the filtered ECG signals, and analyzing the one or more HRV parameters, amplitudes of the filtered respiratory signals and frequencies of the filtered respiratory signals using a predetermined drowsiness detection algorithm to determine the drowsiness state of the driver.

In accordance with a further aspect of the present disclosure, the acceleration signals of the vehicle are measured by one or more triaxial accelerometers.

In accordance with a further aspect of the present disclosure, in order to reduce the motion artifacts on the ECG signals and the respiratory signals based on the acceleration signals, one or more adaptive filtering methods and one or more digital filtering methods. The one or more adaptive filtering methods comprise using one or more adaptive filters, and the one or more digital filtering methods comprise using one or more finite impulse response (FIR) filters, infinite impulse response (IIR) filter, or Kalman filter.

In accordance with a further aspect of the present disclosure, in order to extract one or more HRV parameters from the ECG signals for analyzing and determining whether the driver is drowsy, power spectrum analysis is performed on the RR interval of the ECG signals. The HRV parameters comprise one or more parameters selected from the group consisting of a high frequency (HF) index, a low frequency (LF) index, and an LF/HF ratio.

In accordance with a further aspect of the present disclosure, the step of analyzing the one or more HRV parameters and the respiratory signals using the predetermined drowsiness detection algorithm further comprises the steps of determining, by the one or more processors, a probability model and/or a threshold value of the LF/HF ratio based on one or more biometrical parameters of the driver; determining, by the one or more processors, a probability model and/or a threshold value characterizing the respiratory signals based on one or more biometrical parameters of the driver; and storing, by one or more memory elements in a training module, the probability model and/or the threshold value of the LF/HF ratio and the probability model and/or the threshold value characterizing the respiratory signals. The predetermined drowsiness detection algorithm determines a LF/HF ratio condition by comparing the LF/HF ratio with the probability model and/or the threshold value of the LF/HF ratio; and a respiratory condition by comparing the filtered respiratory signals with the built-in respiratory dataset in the training module; whereby the drowsiness state of the driver is determined based on the LF/HF ratio condition and the respiratory condition.

In accordance with a further aspect of the present disclosure, the biometrical parameters of the driver comprise one or more parameters selected from the group consisting of an age, a gender, a body mass index (BMI) and a race group of the driver.

In accordance with a further aspect of the present disclosure, the in-vehicle monitoring and intervention system comprises one or more processors and an apparatus, wherein the apparatus comprises one or more ECG sensor, at least one respiratory sensor, and at least one filter. The apparatus may further comprise one or more triaxial accelerometers, and an intervention module wherein the intervention module further comprises a transmission module for sending an in-vehicle warning or a smartphone warning. The one or more processors are configured to execute a method of processing ECG signals, respiratory signals and acceleration signals for determining a drowsiness state of a driver.

In accordance with a further aspect of the present disclosure, the one or more ECG sensors are being spaced from each other by a predetermined distance along the seat belt.

In accordance with a further aspect of the present disclosure, the one or more respiratory sensors are positioned on a seat belt for measuring the respiration pattern of the driver. In certain embodiments, the apparatus further comprises a clip for attaching the apparatus to a seat belt of the vehicle as a discrete hardware apparatus. In certain alternative embodiments, the apparatus is integrated into a seat belt of the vehicle using a flexible PCB and a plurality of sensors sewed onto the seat belt.

The details of one or more implementations of the present disclosure are set forth in the accompanying drawings and from the following detailed descriptions. Other features, structures, characteristics, and advantages of the present disclosure will be apparent from the description and drawings, and from the claims.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

Figure 1:
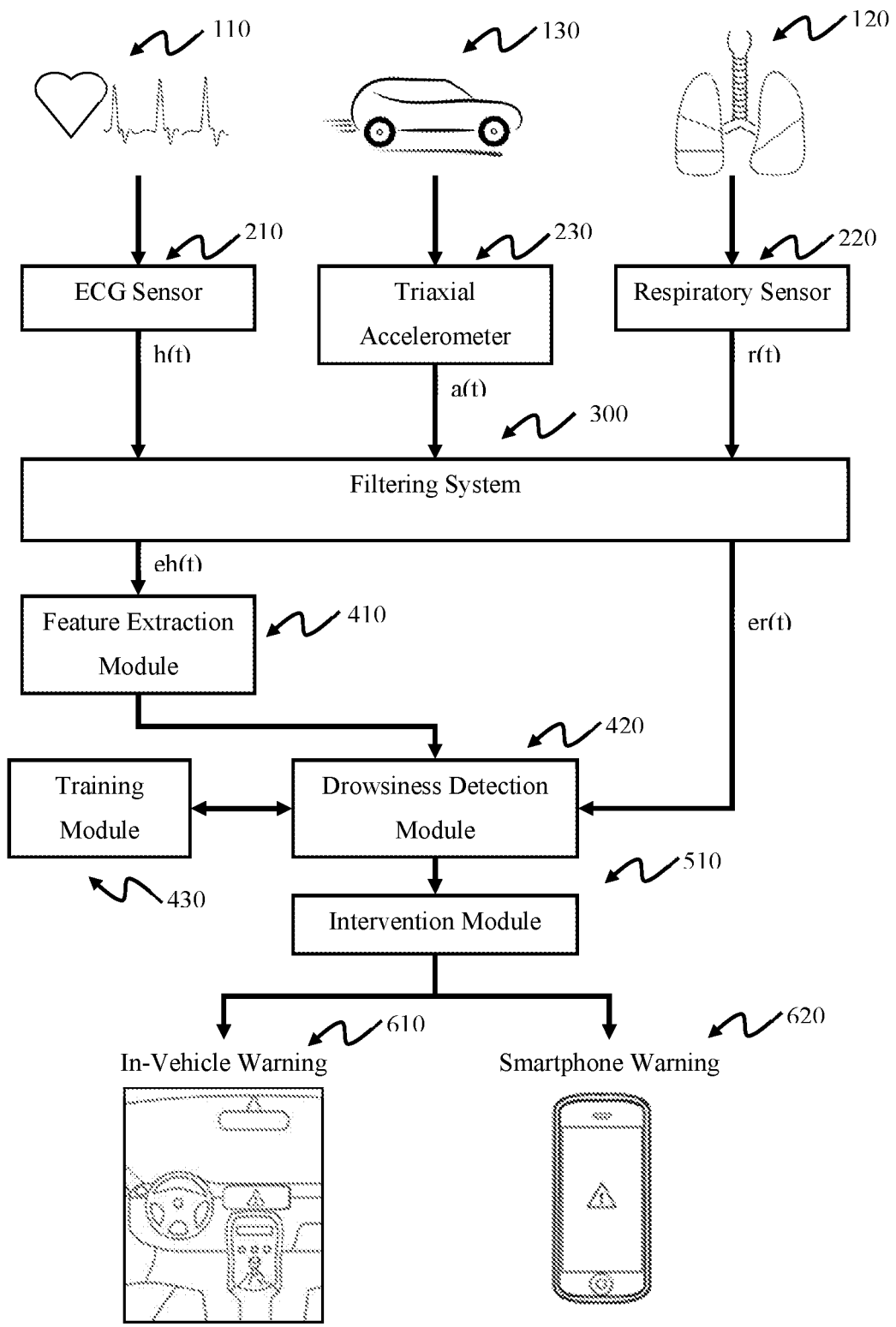
FIG. 1 is a block diagram showing, in outline, the overall structure of an in-vehicle monitoring and intervention system in accordance with certain embodiments of the present disclosure.

Skilled artisans will appreciate that elements in the figures, particularly those conceptual diagrams, are illustrated for simplicity and clarity and have not necessarily been depicted to scale.

DETAILED DESCRIPTION

The following detailed description is merely exemplary in nature and is not intended to limit the disclosure or its application and/or uses. It should be appreciated that a vast number of variations exist. The detailed description will enable those of ordinary skilled in the art to implement an exemplary embodiment of the present disclosure without undue experimentation, and it is understood that various changes or modifications may be made in the function and arrangement of steps and method of operation described in the exemplary embodiment without departing from the scope of the present disclosure as set forth in the appended claims.

The present disclosure relates to an in-vehicle monitoring and intervention system. The following terms are used herein in the specification and appended claims. The term "vehicle" as used herein includes, but is not limited to, a car, a bus, a truck, a train, a cable car, a ship, a ferry, a vessel, an airplane, a helicopter, etc. A "driver" as used herein may therefore include a ship captain, a pilot, etc.

The term "electrocardiogram" or "ECG" as used herein refers to a procedure or a device in which electrical activity of the heart is detected using electrode(s) placed proximate to the heart of the driver, but preferably do not require direct contact with the skin of the driver.

The term "heart rate variability" or "HRV" as used herein is a physiological phenomenon of variation in the time interval of the autonomic nervous system activity of the heart. By extracting RR intervals from the ECG signals and performing power spectral analysis thereto, the ECG signal can be separated into one or more HRV parameters, including a high frequency (HF) index, a low frequency (LF) index and a very low frequency (VLF) index. Unless otherwise stated or indicated, the HF is in the range from 0.15 Hz to 0.4 Hz of the RR intervals, the LF is in the range from 0.04 Hz to 0.15 Hz of the RR intervals, and the VLF is in the range from 0.003 Hz to 0.04 Hz of the RR intervals. The term "LF-HF ratio" as used herein represents a measurement of sympathovagal balance.

The term "microcontroller" or "MCU" as used herein includes central processing units, microprocessors, microcomputers, single-chip computers, cloud computing system, integrated circuits and the like, and systems incorporating the same.

The term "smartphone" as used herein includes any mobile devices such as mobile phone, tablet, phablet, smartwatch, or other portable devices with an associated operating system (IOS, Android, etc) capable of running programmed applications and communicating with the present in-vehicle monitoring and intervention system.

The term "app" as used herein is an abbreviation for the term "application software" and means a software program that can run on a smartphone designed to perform certain tasks or functions by itself, in combination with, and/or as a compliment to another software application.

It should be understood that, throughout the specification and claims herein, when it is described that an element is "coupled" or "connected" to another element, the element may be "directly coupled" or "directly connected" to the other element or "coupled" or "connected" to the other element through a third element. In contrast, it should be understood that, when it is described that an element is "directly coupled" or "directly connected" to another element, there are no intervening elements. The connection between elements may be physical, logical, electrical or any combination thereof.

Section A briefly introduces the method for detecting whether a driver in a vehicle is drowsy based on a plurality of physiological signals of the driver and the overall structure of the in-vehicle monitoring and intervention system. Section B presents the filtering system for suppressing noise and reducing motion artifacts. Section C further demonstrates how to determine the drowsiness condition of the driver. Section D explains the structure of the apparatus for performing in-vehicle monitoring and intervention. Section E provides an exemplary measurement result to demonstrate the application of the in-vehicle monitoring and intervention system.

A. The Overall Structure of the in-Vehicle Monitoring and Intervention System In a broad sense, the present disclosure provides an in-vehicle monitoring and intervention system for determining a drowsiness state of a driver in a vehicle, including one or more ECG sensors 210, one or more respiratory sensors 220, a triaxial accelerometer 230, a filtering system 300 comprising one or more filters, a feature extraction module 410, a drowsiness detection module 420, a training module 430, and an intervention module 510. The term "sensor" is used to represent the ECG sensor 210, respiratory sensor 220 and acceleration sensor 230 generally and collectively. The term "filter" is used to represent the signal filters 311, 312, the adaptive filters 331, 332 and the finite impulse response (FIR) filters 341, 342 generally and collectively. In certain embodiments, the filtering system 300 comprises one or more filters for suppressing noise and eliminating motion artifact from the movement of the vehicle, the driver or both.

When a person is driving a vehicle, it is crucial for the person to buckle up a seat belt 510. The seat belt 510 is designed to reduce the impact force on the driver in case of a collision or an abrupt stop of the vehicle. Therefore, the seat belt 510 can prevent death or injury in accidents. As the seat belt 510 is the only thing that constantly in direct contact with the driver's body, it can be used for more preventive functions other than the conventional life-saving purpose in the situation of an accident. Therefore, the present disclosure provides a method for determining the mental states of the driver by measurement of the heartbeat 110 at (S210) and the respiration pattern 120 at S220 of the driver with the sensors on the seat belt 510 and performing intervention or alert to the driver before any danger is materialized. Such a system is designed to monitor the heart rate and provides alert when the driver may fall asleep at the wheel. Furthermore, motion sensor, e.g., triaxial accelerometer 230, is also integrated into the seat belt 510 for measuring the vehicle motion 130 at (S230) to substantially reduce any inaccuracy caused by the motion artifacts.

Now referring to FIG. 1, there is shown a block diagram of the overall structure of an in-vehicle monitoring and intervention system in accordance with certain embodiments of the present disclosure. The sensors in the system detect a plurality of physiological signals of a driver in a vehicle. In the present disclosure, the physiological signals mean the heartbeat 110 and the respiration pattern 120 of the driver. As a result, the in-vehicle monitoring and intervention system can determine the mental state of the driver based on the measurement of the heartbeat 110 and the respiration pattern 120 with a predetermined drowsiness detection algorithm.

One or more non-contact electrocardiogram (ECG) sensors 210 have been developed for cardiac monitoring of a person using non-contacting sensing electrode through the clothing without direct contact with the skin of the driver. In certain embodiments of the present disclosure, two or more ECG sensors 210 are placed on a seat belt 510 for measuring the heartbeat 110 of the driver (S210) to obtain a continuous and periodic measurement of the ECG signals h(t). The one or more of sensors is placed at various locations proximate to the driver's heart with a predetermined separation for improved quality on the measurements acquired. In order to improve the QRS complex of the acquired ECG signal h(t), the ECG sensors are being spaced from each other by at least 10 cm distance along the seat belt.

The respiratory sensor 220 allows a measurement of the inhale and exhale of the driver. The use of nasal sensors and oral sensors for measuring the airflow or air volume are possible but not practicable for the purpose of general monitoring of a driver's physiological signals. In the present disclosure, one or more respiratory sensors 220 are placed on the seat belt for capturing the body movement during inhaling and exhaling. Each sensor can be an abdominal respiratory motion tracker placed in the regions proximate to the thorax or the abdomen of the driver such that the respiration pattern 120 of the driver can be monitored continuously at a constant sampling rate. In one embodiment, the constant sampling rate is 128 samples per second. This provides the respiratory signals r(t) for further analysis. The respiratory characteristics include the waveform, the amplitude, the frequency, inspiration and expiration slope, etc. of the respiratory signals.

The triaxial accelerometer 230 measures the vehicle motion 130 and tracks the acceleration signal a(t) for improving the accuracy on the acquired ECG signals h(t) and the acquired respiratory signals r(t). This can substantially reduce motion artifacts which may be produced by the movement or change of speed of the vehicle. In certain embodiments, other motion detecting devices, including 3-axis gyro sensor, angular position sensor, digital angle sensor, 1-axis accelerometer, 2-axis accelerometer, 4-axis accelerometer, 5-axis accelerometer, 6-axis accelerometer and the like, or other vehicle monitoring system, including in-vehicle speed monitoring system, car speedometer, apparatus using the global positioning system (GPS), and the like are used by the present disclosure for acquiring the acceleration signal a(t).

In order to effect accurate measurement of the ECG signals h(t) and the respiratory signals r(t), noise filtering S310 is indispensable. The present disclosure utilizes a filtering system 300 to suppress noise and perform adaptive motion artifact cancellation. The filtering system 300 comprises one or more filters selected from the group consisting of signal filters 311, 312, adaptive filters 331, 332 and FIR filters 341, 342. In certain embodiments, the filtering system 300 and the filters therein may be discrete components or implemented by a microcontroller unit (MCU), a custom integrated circuit, a field-programmable gate array (FPGA), other semiconductor devices, or any suitable combination of the foregoing.

Figure 2:
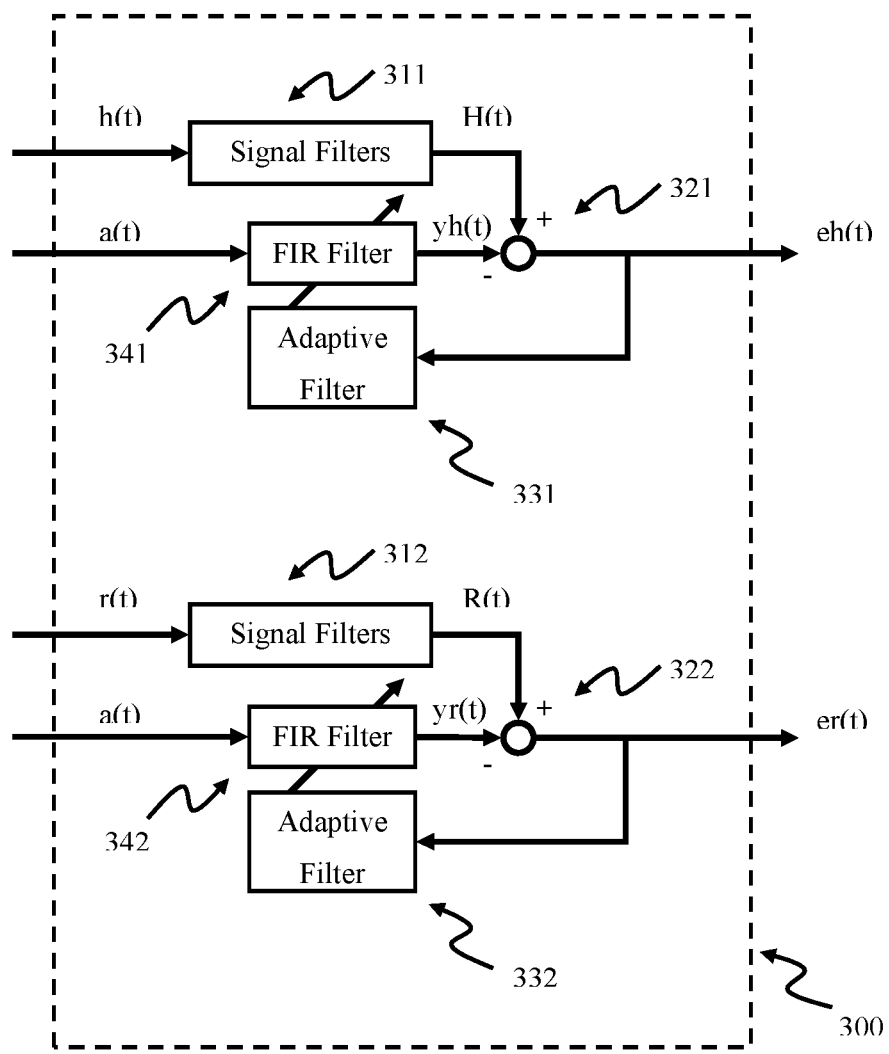
FIG. 2 is a block diagram showing the filtering system in accordance with certain embodiments of the system disclosed in FIG. 1.
Figure 3:
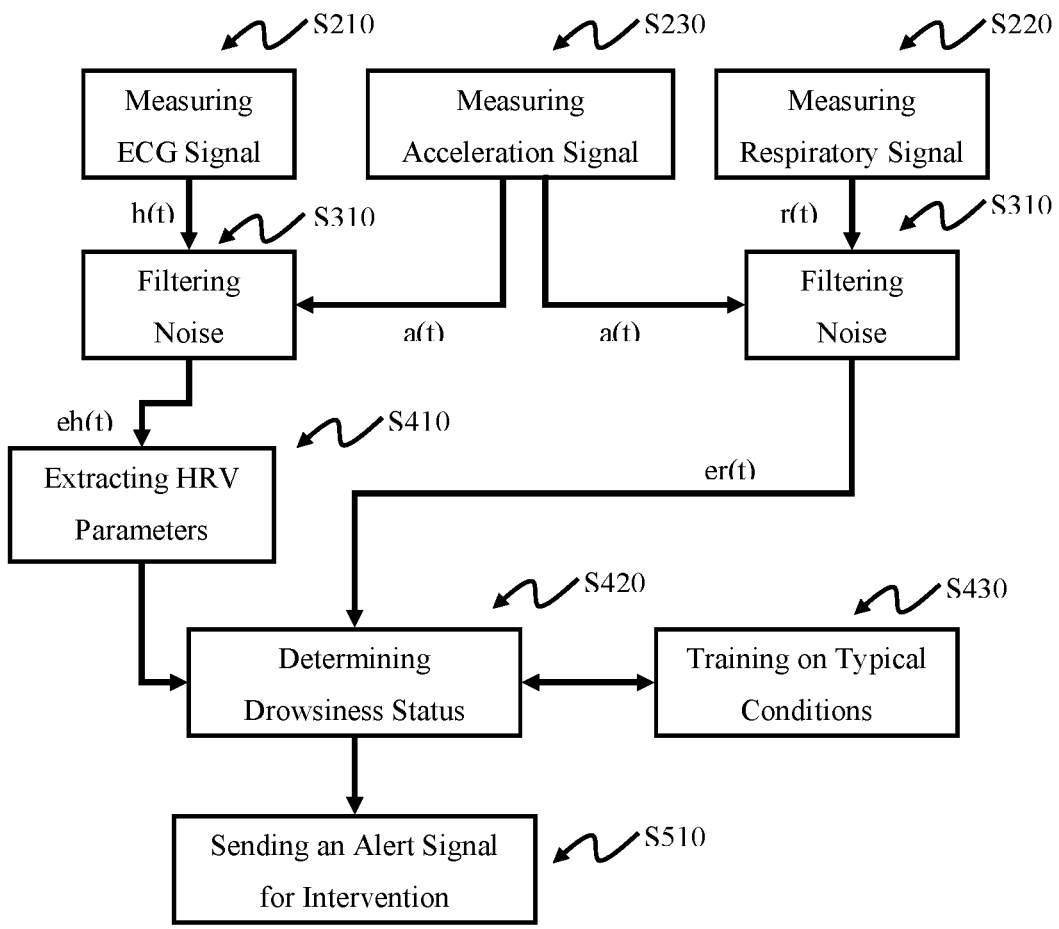
FIG. 3 is a flowchart showing a method for detecting whether a driver in a vehicle is drowsy in accordance with certain embodiments of the present disclosure.

As shown in FIG. 2, a block diagram illustrating the filtering system 300 is depicted. A signal filter 311 is used to perform the first stage of noise filter on the incoming ECG signal h(t), and another signal filter 312 is used to perform the first stage of noise filtering on the incoming respiratory signal r(t). The two signal filters 311, 312 can be implemented by using a bandpass filter, bandstop filter or a notch filter with 50/60 Hz for selecting the frequency range to be extracted. The signal filters 311, 312 enable suppression of other noise signals or harmonics at higher or lower frequencies. The center frequency can be adjusted or tuned, and the bandwidth can be adjusted or tuned according to the actual situations in the corresponding applications. In certain embodiments, the signal filter 311 for the ECG signals has a spread of 0.5 Hz to 40 Hz for obtaining H(t). The signal filter 312 for the respiratory signals has a spread of 0.1 Hz o 10 Hz for obtaining R(t). The signal filters 311, 312 can use other frequency ranges without departing from the scope or spirit of the present invention.

As heart rate variability (HRV) is particularly sensitive to artifacts, which will result in significant errors in determining the drowsiness condition of the driver. It is important to eliminate unwanted elements in the ECG with respect to the motion of the vehicle. Similarly, the same filtering system for noise elimination can also be used in the respiratory signals for improving the signal quality. In the present disclosure, a combination of an adaptive filter 331 and an FIR filter 341 is used to substantially reduce motion artifacts or other electrophysiological signals on the ECG signals H(t). The acceleration signal a(t) correlates to the motion artifact and is used to compensate the movement of the vehicle. Similarly, a combination of an adaptive filter 332 and an FIR filter 342 is used to substantially reduce motion artifacts or other electrophysiological signals on the respiratory signals R(t). The filtered ECG signals eh(t) and the filtered respiratory signals er(t) are transmitted to and used in the feature extraction module 410 and drowsiness detection module 420 for extracting one or more HRV parameters and determining the drowsiness condition of the driver.

Now referring back to FIG. 1, the filtered ECG signals eh(t) are transmitted to and processed by a feature extraction module 410 for extracting RR intervals (S411) from the filtered ECG signals; and performing power spectrum analysis on the RR intervals for extracting the one or more HRV parameters from the filtered ECG signals (S410), preferably in both time domain and frequency domain. In particular, the HRV parameters comprise one or more parameters selected from the group consisting of a high frequency (HF) index (S412), a low frequency (LF) index (S413) and a very low frequency (VLF) index. In certain embodiments, other parameters and indexes may be extracted (S414), e.g., the standard deviation of normal to normal (NN) intervals index (SDNN), the square root of the mean of the sum of the squares of differences between adjacent NN intervals (RMSSD), the standard deviation of differences between adjacent NN intervals (SDSD), the number of pairs of adjacent NN intervals differing by more than 50 ms in the entire recording (NN50), the NN50 count divided by the total number of all NN intervals (PNN50), or any suitable combination of the foregoing. These HRV parameters and the filtered respiratory signals er(t) are used by the drowsiness detection module 420 for subsequent mental state determination.

The mental state determination S420 means identifying the state of awareness or drowsiness of the driver through analyzing a plurality of physiological signals, including the HRV parameters and the respiratory signals, with a predetermined drowsiness detection algorithm. The method for determining the drowsiness condition of the driver is discussed in section C of the present disclosure.

In certain embodiments, the in-vehicle monitoring and intervention system can include a training module 430 for storing and tracking the trend of the measured physiological signals of a particular driver. The training module 430 includes one or more memory elements. The memory elements store the threshold values of the one or more HRV parameters, the threshold values of the amplitudes of the respiratory signals and the threshold values of the frequencies of the respiratory signals of the driver in the array of memory cells. In certain embodiments, the memory cells can be a device readable storage medium such as a non-transitory storage device. A memory cell may be, e.g., a digital memory, a magnetic storage medium, optical readable digital data storage medium, semiconductor device, or any suitable combination of the foregoing. More specific examples of the storage device would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. The one or more processors calculate the threshold values of the one or more HRV parameters, the threshold values of the amplitudes of the respiratory signals and the threshold values of the frequencies of the respiratory signals of the driver based on the filtered ECG signals eh(t) and the filtered respiratory signals er(t).

The intervention module 510 receives signal from the drowsiness detection module 420 when the driver in a vehicle is determined to be drowsy. By sending an alert signal for intervention S510, preferably to the dashboard in the vehicle 610 or the connected smartphone 620 via Bluetooth or other wireless communication technologies, the driver can be warned of the danger with an attempt to wake the driver from being drowsy.

In certain embodiments, the filtered ECG signals eh(t) and the filtered respiratory signals er(t) are digitized and transmitted by a transmission module to a smartphone for extracting HRV parameters (S410), determining drowsiness status (S420) and sending an alert signal for intervention (S510). The app in the smartphone is designed to receive the transmitted signals from the seatbelt or discrete hardware apparatus with a feature extraction module 410, a drowsiness detection module 420, a training module 430 and an intervention module 510 within. The app can determine the drowsiness condition and send out in-vehicle warning 610 or smartphone warning 620 by the transmission module in the intervention module 510 (S510).

In certain alternative embodiments, the feature extraction module 410, the drowsiness detection module 420, the training module 430 and the intervention module 510 can be integrated and encompassed within a microcontroller unit (MCU), a custom integrated circuit, a digital signal processors (DSP), a field-programmable gate array (FPGA), an application specific integrated circuits (ASIC), a programmable I/O device, other semiconductor devices, or any suitable combination of the foregoing of the apparatus. The apparatus can determine the drowsiness condition and send out in-vehicle warning 610 or smartphone warning 620 by the transmission module in the intervention module 510 (S510).

B. The Filtering System for Suppressing Noise and Reducing Motion Artifacts

The structure of the filtering system 300 is depicted in FIG. 2. The purpose of the filtering system 300 is to suppress noise and eliminate motion artifact from the movement of the vehicle, the driver or both. With a closer look at the motion artifact caused by the movement of the vehicle, we can assume that the motion of the driver can trigger the triaxial accelerometer 230, gives EQN. (1):

$$a(t) = \begin{bmatrix} a_x(t) \\ a_y(t) \\ a_z(t) \end{bmatrix} \tag{1}$$

$$y(t) = w_x(k) \cdot a_x(t) + w_y(k) \cdot a_y(t) + w_z(k) \cdot a_z(t) \tag{2}$$

From EQN. (2), y(t) is a signal output from the FIR filter 341, 342, and it is denoted as yh(t) for the case of ECG signals, and yr(t) for the case of respiratory signals. Since the acceleration signal a(t) correlates to the motion artifact, we can deduce the weight $[w_x(k)\ w_y(k)\ w_z(k)]$ individually for heartbeat and respiration, where w_(k) is a 1×M matrix, such that:

$$H(t)-yh(t)=eh(t) \tag{3}$$

$$R(t)-yr(t)=er(t) \tag{4}$$

Both eh(t) and er(t) are relatively clean ECG signals and respiratory signal.

The adaptive filters 331, 332 as used herein may be implemented by a least mean squares (LMS) adaptive filter, recursive least squares (RLS) adaptive filter, or a gradient adaptive laguerre-lattice (GALL) filter.

B1. LMS Adaptive Filter

By using an LMS adaptive filter, the difference between the desired signal and the actual measured signal is used to determine the optimized filter coefficients. In order to obtain a clean ECG signal, we have to minimize the cost function J(t) using the EQN. (5):

$$J(t) = \frac{1}{2}e^2(t) \tag{5}$$

By applying the stochastic gradient descent method, we can obtain EQN. (6):

$$\frac{\partial J(t)}{\partial w_m} = -e(t)a(t-k) \tag{6}$$

By moving on from $w_m$ to $w_{m+1}$ by an amount proportional to $$\frac{\partial J(t)}{\partial w_m},$$

we can obtain EQN. (7):

$$w_{m+1}=w_m+\mu e(t)a(t-k) \tag{7}$$

wherein:

μ is an arbitrary value of about 0.1 to 0.0001;

m is an index referring to the filter element; and

J is the cost function, which represents the amount of discrepancy of the desired signal and y.

B2. RLS Adaptive Filter

An alternative approach of using an RLS adaptive filter can provide a similar effect by recursively finding the coefficients that can minimize a weighted linear least squares cost function in relation to the ECG signals H(t) and the respiratory signals R(t), which are both considered to be deterministic.

$$y(t) = \sum_{k=0}^{M-1} b_k a(t) \tag{8}$$

$$\varepsilon(t) = \sum_{i=0}^{t} \lambda^{n-i} e^2(i) = \sum_{i=0}^{t} \lambda^{n-i}(d(i)-y(i))^2 \tag{9}$$

$$k(t) = \frac{R^{-1}(t-1)a(t)}{\lambda + a^T(t-1)R^{-1}(t-1)a(t)}; \text{ and} \tag{10}$$

$$R^{-1}(t) = \lambda^{-1}[R^{-1}(t-1) - k(t)a^T(t)R^{-1}(t-1)] \tag{11}$$

As a result, the filter coefficient can be deduced as:

$$b(t)=b(t-1)+k(t)\varepsilon(t) \tag{12}$$

wherein:

b(t) is a filter coefficient;

λ is the forgetting factor;

a(t) is the input noisy signal;

ε(t) is an error filtered signal.

B3. GALL Filter

Figure 4:
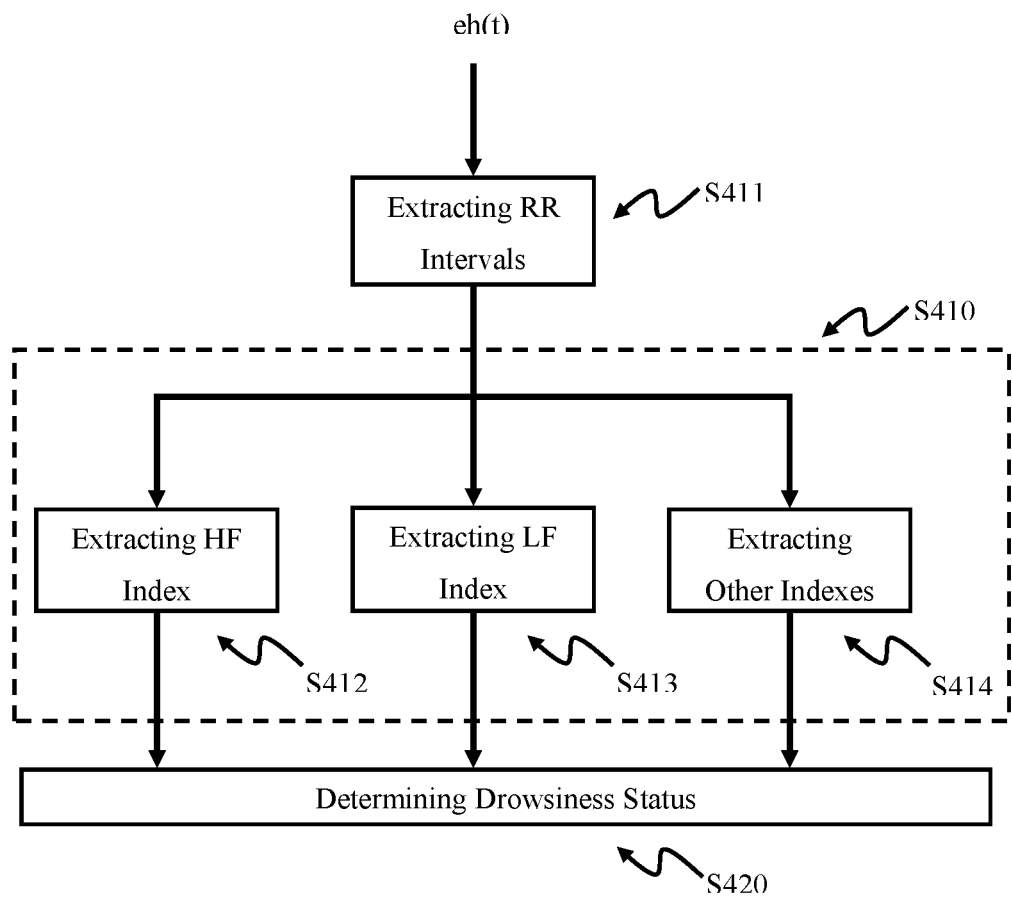
FIG. 4 is a flowchart showing a method for extracting features from an ECG signal after noise filtering in accordance with certain embodiments of the system disclosed in FIG. 3.

For the case of using GALL filter, the structure of a conventional GALL filter as disclosed in FIG. 4 of [1] and table I of [2] can be applied. The GALL filter can effectively reduce the motion artifact component of respiratory signals and the signal quality can be improved.

In one embodiment, the GALL filter is used to filter the ECG signal.

C. Determining the Drowsiness Condition of the Driver

In order to determine the drowsiness condition of a driver, the feature extraction module 410 is programmed to extract RR intervals (S411) from the filtered ECG signals eh(t) and perform both time-domain analysis and frequency-domain analysis for extracting the one or more HRV parameters (S410). In a typical ECG signal, different patterns are carrying useful information for identifying the mental state of the driver, including P-wave, QRS complex, T-wave and U-wave. In order to obtain an accurate measurement, the pattern recognition of the ECG signal is particularly important. The feature extraction module 410 can first obtain the RR interval by analyzing the ECG signal with a non-linear method, which is calculated based on the time interval of two successive R peaks of the ECG signal.

By performing time-domain analysis, the feature extraction module 410 can obtain one or more HRV parameters or other indexes (S414), including SDNN, RMSSD, SDSD, NN50 and PNN50. SDNN is the standard deviation of the average NN intervals calculated over short periods, usually 5 minutes. RMS SD is the square root of the mean of the squares of the successive differences between adjacent NNs. SD is the standard deviation of the successive differences between adjacent NNs. NN50 is the number of pairs of successive NNs that differ by more than 50 ms. PNN50 is the proportion of NN50 divided by total number of NNs.

By performing frequency domain analysis on the RR interval, the feature extraction module 410 can obtain the count of the number of NN intervals at each frequency bands, which typically includes the HF, LF and VLF, thereby allowing the calculations of the normalized high frequency (nHF), normalized low frequency (nLF) and the LF to HF ratio (LF/HF), as follow:

$$nHF = HF/(TP-VLF)*100 \quad (13)$$

$$nLF = LF/(TP-VLF)*100 \quad (14)$$

$$LF/HF = \frac{LF}{HF} \quad (15)$$

$$HF\% = 100*HF/(LF+HF) \quad (16)$$

The LF/HF and HF % are the major factor for determining the drowsiness condition of the driver as it changes significantly when the driver enters a sleeping cycle from a conscious state. If the driver does not have a sufficient sleep, e.g., less than 4 hours of sleep during the night before, the driver may have a significantly higher value in HF % than the corresponding HF % with sufficient sleep. Therefore, the LF and HF indexes can be used to deduce a plurality of threshold values for identifying whether the driver has a sufficient sleep. In certain embodiment, the HF % is particularly used to classify whether a person has a sufficient sleep.

However, all the HRV indices may vary substantially for different drivers. Factors including age, gender, body mass ratio (BMI), and race group of the driver may affect all HRV indices. In view of the wide variation of all HRV indices, classification with respect to the personal factor is employed for determining a specific threshold value for each driver based on a training data.

Advantageously, the present disclosure utilizes a predetermined testing group distribution for determining the normal distribution of each HRV parameter and respiratory parameter for each driver. As it is identified that male drivers have a significantly higher LF/HF than female drivers, and the age of the driver has a reverse relationship with the LF/HF. Therefore, it is possible to obtain a classification by characterizing the variations. The probability model and/or the threshold value obtained can provide a range of typical conditions of a specific group of drivers, and an individual driver in that group is presumed to follow a normal distribution. Furthermore, with the probability model and/or the threshold value identified, the training module 430 can make a fine adjustment on the distribution to reflect the individual biometrical conditions for further improving the accuracy.

In certain embodiments, the training module 430 stores the patterns of various biometrical parameters, e.g., the HF index, LF index, the LF/HF and other respiratory parameters at different drowsiness states, wherein the LF/HF is the most critical parameter for determining the drowsiness state of the driver. The training module identifies the drowsiness state to which the driver belongs to and correlates the biometrical parameters, particularly the initially recorded HRV indices. The drowsiness state of the driver will be used to activate the alarm function based on the probability of the drowsiness state, namely a probabilistic alarm function.

Figure 8:
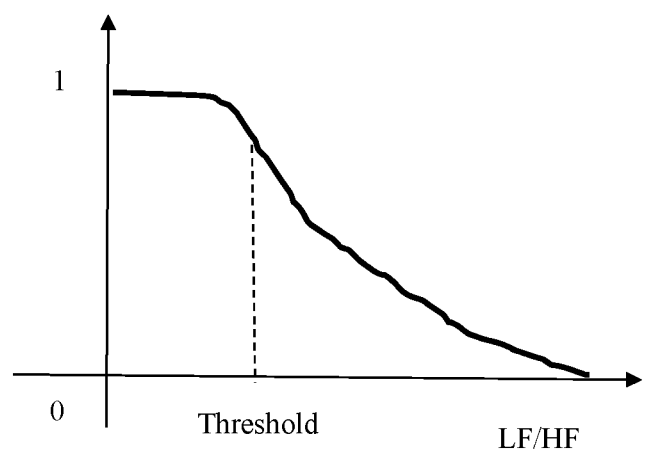
FIG. 8 is a graph depicting the relationship between the probabilistic alarm function and the LF/HF ratio in accordance with certain embodiments of the present disclosure.

The drowsiness detection module 420 analyses the relationship between the drowsiness state of the driver from the training module 430 with the measured HRV parameters and measured respiratory parameters. An LF/HF condition is determined by comparing the measured LF/HF with the LF/HF in the training dataset, as demonstrated in FIG. 8. When the probabilistic alarm function is 1, the driver is expected to be in drowsy condition and it is necessary to alert the driver. In one embodiment, there is a threshold value predetermined, such as 0.7, so that when the probabilistic alarm function is equal to or higher than the threshold value, the driver will be alerted. In such a method, the LF/HF is used to signify, when comparing to the data in the training module 430, how likely the driver is in the sleepy stage. Whether to alarm or not is determined in accordance with the probabilistic alarm function as obtained from the training module 430. In the alarm function, certain LF/HF will give a corresponding probability value.

On the other hand, a respiratory condition is determined based on the correlation r, of the respiration signal with the drowsy respiration signal, calculated to deduce the probabilistic alarm function. The curve for the probabilistic alarm function is formed by the parameters as shown in EQN. (17) below:

$$r_{xy} = \frac{\sum_{i=1}^{n}(x_i - \bar{x})(y_i - \bar{y})}{\sqrt{\sum_{i=1}^{n}(x_i - \bar{x})^2} \sqrt{\sum_{i=1}^{n}(y_i - \bar{y})^2}} \quad (17)$$

wherein:
x is the build-in respiratory signal dataset; and
y is the newly recorded respiratory data.

The closer the parameters of the respiration signal to the threshold value of the alarm function, the higher the chance the alarm function will trigger the warning. Similarly, a machine learning algorithm may also be applied for the drowsiness detection, while the input parameters to the machine learning model are the physiological parameters of a driver as discussed above.

To improve the performance of the drowsiness detection, big data analytics may be adapted to gather data from users with similar biometrical parameters, including HRV indices and respiratory indices, through the networks by the mobile apps. Other personal information including age, gender, BMI, eating habit, sleeping habit, intake of drugs and workloads in that day may also be the parameters in the machine learning algorithm. Together with the aforesaid machine learning algorithm, the system can more accurately estimate the drowsiness state of a driver.

Figure 5:
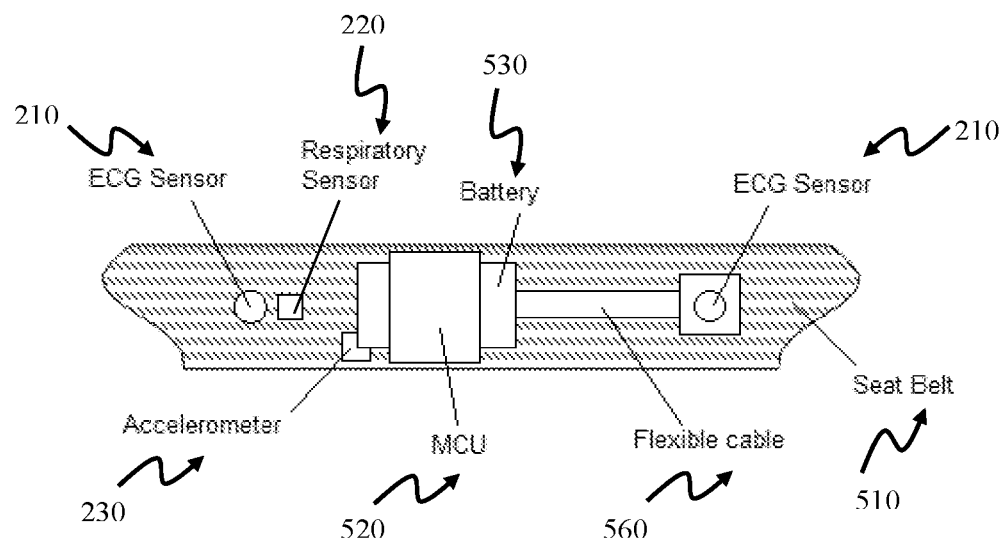
FIG. 5 is a top view of an in-vehicle monitoring and intervention apparatus integrated into a seat belt in accordance with certain embodiments of the present disclosure.
Figure 6:
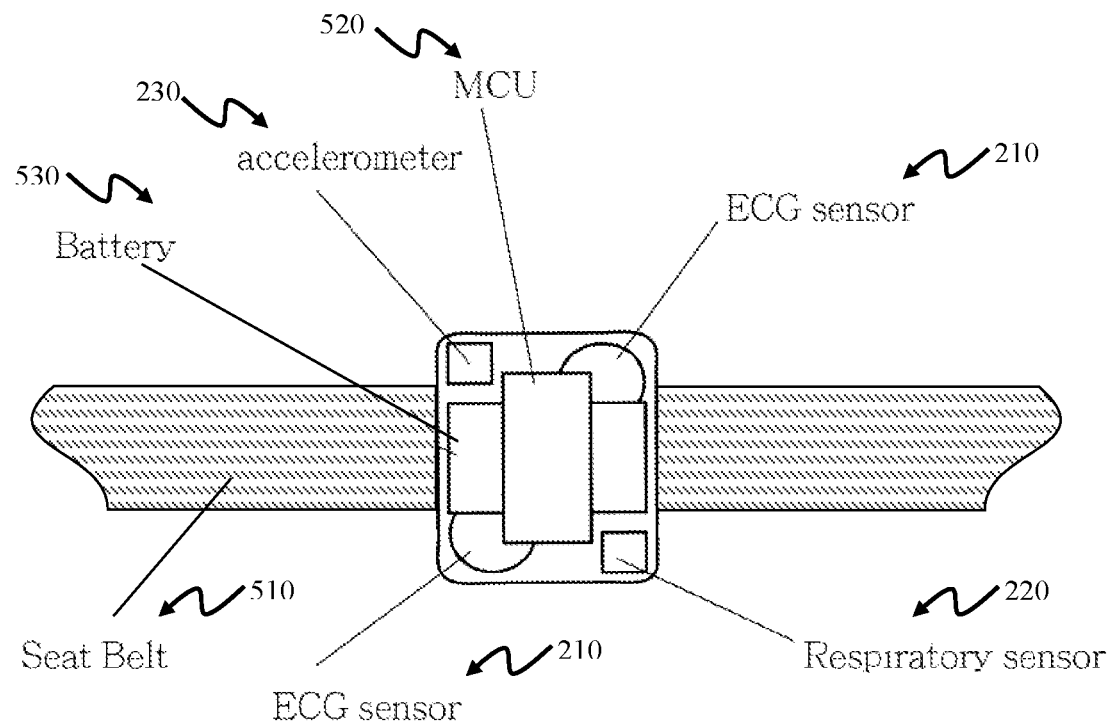
FIG. 6 is a top view of an in-vehicle monitoring and intervention system as a discrete hardware apparatus that can be attached to a seat belt in accordance with certain embodiments of the present disclosure.
Figure 7:
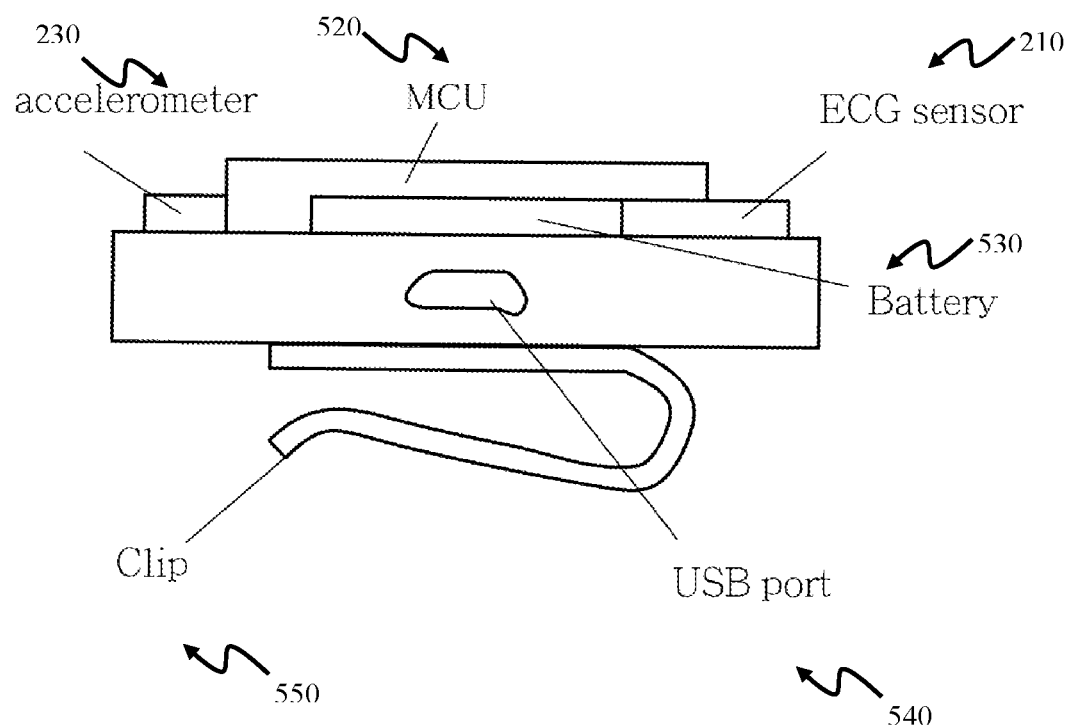
FIG. 7 is a side view of the apparatus of FIG. 6.

D. Structure of the Apparatus for Performing in-Vehicle Monitoring and Intervention FIGS. 5-7 show different views and structures of the apparatus for performing in-vehicle monitoring and intervention according to an embodiment of the present disclosure. FIG. 5 is an exemplary system integrated into a seat belt 510, while FIG. 6 and FIG. 7 demonstrate a discrete hardware apparatus that can be attached to a seat belt 510.

The in-vehicle monitoring and intervention system may comprise one or more processors and an apparatus, wherein the apparatus comprises one or more ECG sensors 210, one or more respiratory sensors 220, an accelerometer 230, an MCU 520, a battery 530, a Universal Serial Bus (USB) port 540, a clip 550 and a flexible cable 560. The MCU 520 may further comprise other circuitry for performing noise or motion artifact filtering and wireless communication.

FIG. 5 illustrates certain embodiments of the apparatus integrated into a seat belt 510. There are two ECG sensors 210, wherein one of them is connected to the MCU 520 with a flexible cable 560. The flexible cable 560 allows extensive flexibility in adjusting the position of the ECG sensor 210 such that the system can fit persons of different body size. The other ECG sensor 210, the respiratory sensor 220 and the accelerometer 230 may be integrated to the seat belt 510 and connected to the MCU 520 with wires, e-textiles or other conductive textiles, such as copper-nylon fabric. This provides an advantage that the seat belt remains flexible while the cable has not bulged. The apparatus is powered by a battery 530.

Alternatively, the apparatus can be a discrete hardware apparatus that can be attached to the seat belt 510, as shown in FIG. 6 and FIG. 7. The ECG sensors 210 are placed diagonally such that the distance apart can be maximized. At the bottom side of the device, there is a clip 550 attached such that the device can be firmly attached to a seat belt 510 and freely moved along the seat belt 510 to a position closer to the driver's heart. In both configurations, the device is also provided with a USB port 540 for charging the battery 530 or transmitting data for the record. The USB port 540 can be a micro USB port, a USB type-C port, mini-USB port, or other types of port connector.

In certain embodiments, the MCU 520 comprises the feature extraction module 410, the drowsiness detection module 420, the training module 430 and the intervention module 510. The physiological signals are processed by the MCU 520 to determine the drowsiness condition of the driver. If it is determined that the driver is drowsy, an in-vehicle warning 610 or smartphone warning 620 is sent out by the transmission module to warn the driver.

In certain alternative embodiments, the MCU 520 only comprises the transmission module. The filtered physiological signals are digitized and transmitted by to a smartphone for further processing. The apparatus and the smartphone may be connected through any type of connection or network, including a local area network (LAN), a wide area network (WAN), or the connection through other devices, e.g., through the Internet using an Internet Service Provider (ISP), through other wireless connections, e.g., near-field communication, or through a hardwire connection, such as a USB connection. In certain alternative embodiments, the smartphone may act as a pass-through device and may further send the filtered physiological signals received from the apparatus to a processor in other devices without processing.

In certain embodiments of the present disclosure, the circuits in the system can be implemented at least partially by software programs, transistors, logic gates, analog circuit blocks, semiconductor devices, other electronic devices, or a combination of any circuit structures described above. Because some of the circuits may be implemented as software, the actual connections and structures may differ depending on the manner in which the software is programmed.

E. An Exemplary Measurement Result

The disclosed method for performing in-vehicle monitoring and intervention is exemplarily demonstrated with the aid of the waveforms in FIG. 9 to FIG. 13, which provide the experimental results at each stage according to one embodiment of the present disclosure. The measurement results provide a set of raw ECG signal and a set of the acceleration signal, as obtained from a non-contact ECG sensor and a 2-axis accelerometer respectively. The ECG sensor and the 2-axis accelerometer are placed on a discrete hardware apparatus of FIG. 6 that can be attached to a seat belt.

Figure 9:
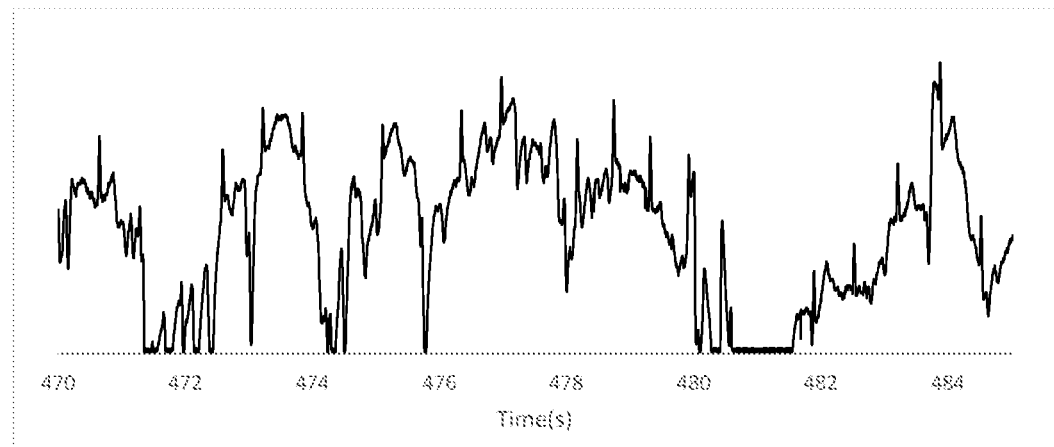
FIG. 9 is an exemplary raw ECG signal acquired by a non-contact ECG sensor.

FIG. 9 is an exemplary raw ECG signal of the driver acquired by an ECG sensor 210. In the present example, one ECG sensor 210 is used to measure the heartbeat 110 of the driver. The raw ECG signal is acquired in a non-contact manner during driver, and the signal baseline fluctuates in amplitude more significant than the amplitude of the ECG pattern of the driver. Therefore, the signal is too noisy and difficult to perform analysis for determining the drowsiness condition of the driver.

Figure 10:
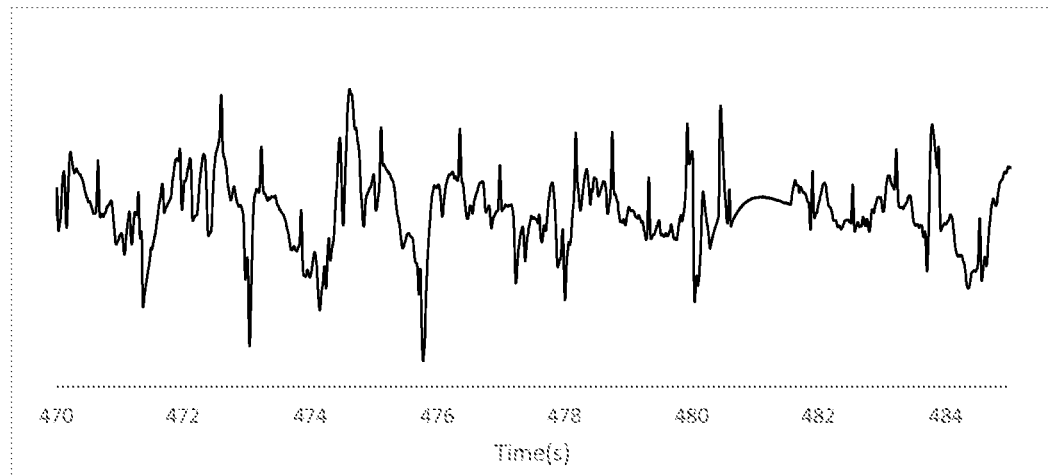
FIG. 10 is a filtered ECG signal of FIG. 9 after performing signal filtering in accordance with certain embodiments of the present disclosure.

In order to perform analysis on the acquired signal, the ECG signal is filtered accordingly. As shown in FIG. 10, a filtered ECG signal is obtained by suppressing noise using a bandpass filter. With reference to the standard deviation of the signal every 10 seconds, it is noted that the filtered ECG signal is a steady signal having a lower standard derivation than the raw ECG signal of FIG. 9. In general, the filter ECG signal has about 20% less standard derivation, and therefore the signal quality is improved. The baseline fluctuation is also reduced in the resulting waveform, but the R-peak is still difficult to be isolated from the motion artifact. In order to extract the R-peak for analysis, further noise reduction is required.

Figure 11:
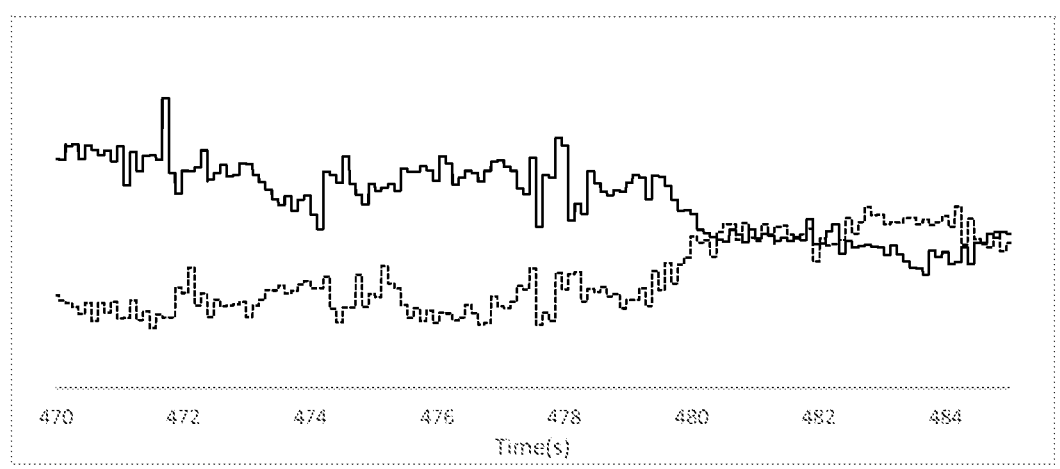
FIG. 11 is 2-axis acceleration signals as measured by a motion sensor when capturing the ECG signal of FIG. 9.

In FIG. 11, the acceleration signals as measured by a 2-axis accelerometer are provided. The 2-axis accelerometer obtains adequate samples every second to capture the 2-dimensional movement of the vehicle. When either one of the acceleration signals shows an abrupt rise or fall in the reading, the vehicle is expected to be experiencing an acceleration or a break. The acceleration signal correlates to the motion artifact and is used to compensate the movement of the vehicle. These signals can be used as a noise source for the adaptive filtering. When the change in acceleration signal does not correlate to any noisy signal, the filtered ECG signal is not compensated. In the exemplary measurement, abrupt accelerations of at least one axis are observed at 471.8 s, 474.2 s, and 477.6-478 s. However, the abrupt acceleration at 471.8 s does not correlate with the motion artifact in the ECG signal and therefore no obvious enhancement is made.

Figure 12:
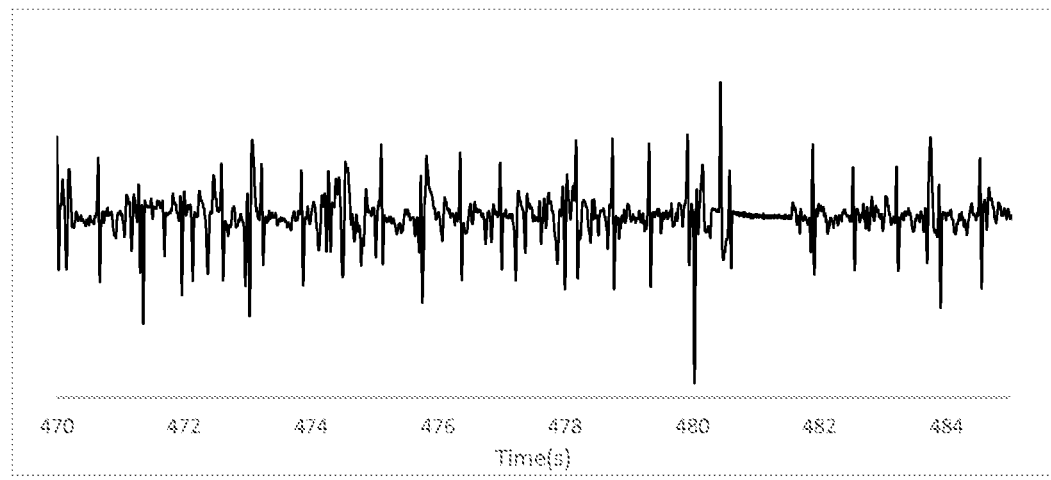
FIG. 12 is an adaptive ECG signal of FIG. 9 after performing adaptive filtering in accordance with certain embodiments of the present disclosure.

After cancellation with the acceleration signal using FIR filter 341 and adaptive filter 331, an adaptive filtered ECG signal is obtained as shown in FIG. 12. The baseline of the waveform is flattened, and the R-peaks become prominent for feature extraction and drowsiness condition determination. In particular, the LF to HF ratio can be extracted using frequency domain analysis on the R-peaks.

Figure 13:
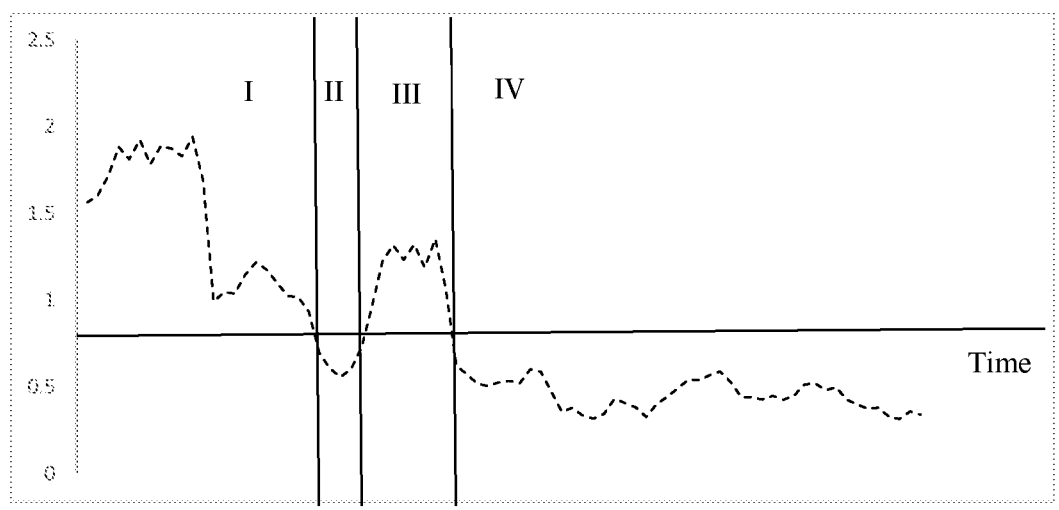
FIG. 13 is an exemplary measurement of the LF/HF ratio of a driver for determining the drowsiness condition of the driver in accordance with certain embodiments of the present disclosure.

The noise and motion artifacts in the raw ECG signal are suppressed, and the resulting adaptive filtered ECG signal is provided to the feature extraction module 410 and the drowsiness detection module 420. In certain embodiments, the major factor for determining the drowsiness level is based on the LF to HF ratio, as provided in EQN. (15). The LF/HF index of the person was monitored from awake to sleep in about one hour, and the variations of the LF/HF index is shown in FIG. 13. During stage I, the person was awake, and the LF/HF ratio was above 0.8. During stage II, the person almost fell asleep with a momentarily drop of LF/HF ratio. In stage III, the person awoke suddenly, and so the LF/HF ratio is increased significantly. Lastly, at stage IV, the person fell asleep again with the LF/HF ratio falls to around 0.5.

As demonstrated in the example above, by setting a threshold value of 0.8, the drowsiness condition of the person can be determined accurately. The threshold will determine whether the person is awake or drowsy. The numerical value of the threshold is expected to deviate for different people, and the range of typical threshold value can be identified based on classification in accordance with the driver's biometric parameters (e.g. gender and age). Furthermore, the training module 430 can make a fine adjustment on the threshold value such that the accuracy of the drowsiness detection can be improved.

It will be apparent to those skilled in the art that various modifications and variations can be made to the structure of the present invention without departing from the scope or spirit of the invention. In view of the foregoing descriptions, it is intended that the invention covers modifications and variations of this invention if they fall within the scope of the following claims and their equivalents.

F. List of References

The following documents are cited in this patent application. References [1]-[2] are incorporated by reference herein.

[1] Zhengbo Zhang, et al., "Adaptive motion artefact reduction in respiration and ECG signals for wearable healthcare monitoring systems", *Medical & biological engineering & computing,* 52:1019-1030, 2014.

[2] Zoran Fejzo et al., "Adaptive Laguerre-lattice Filters", *IEEE Transactions on Signal Processing*, Vol 45, No. 12, December 1997

What is claimed is:

1. A method for determining a drowsiness state of a driver in a vehicle, characterized in that the method comprising:
   a detection process comprising:
      measuring electrocardiogram (ECG) signals of the driver by one or more ECG sensors;
      measuring respiratory signals by one or more respiratory sensors based on a respiration pattern of the driver; and
      measuring acceleration signals of the vehicle, the driver or both;
   a filtering process for performing adaptive motion artifact cancellation comprising reducing motion artifacts on the ECG signals and the respiratory signals based on the acceleration signals to obtain a filtered ECG signal and a filtered respiratory signal respectively; and
   a determination process by a machine learning algorithm comprising:
      extracting one or more heart rate variability (HRV) parameters from the filtered ECG signals; and
      analyzing the one or more HRV parameters and the respiratory signals using a predetermined drowsiness detection algorithm to determine the drowsiness state of the driver.

2. The method according to claim 1, characterized in that the acceleration signals of the vehicle are measured by one or more triaxial accelerometers.

3. The method according to claim 1, characterized in that the filtering process further comprising filtering the ECG signals and the respiratory signals by one or more signal filters for noise suppression.

4. The method according to claim 1, characterized in that the step of reducing motion artifacts on the ECG signals and the respiratory signals based on the acceleration signals comprises the step of filtering motion artifacts of the vehicle, the driver or both using one or more adaptive filtering methods and one or more digital filtering methods.

5. The method according to claim 4, characterized in that the one or more adaptive filtering methods comprise using one or more adaptive filters.

6. The method according to claim 1, characterized in that the step of extracting the one or more HRV parameters from the filtered ECG signals comprises extracting RR intervals from the filtered ECG signals; and performing power spectrum analysis on the RR intervals.

7. The method according to claim 1, characterized in that the one or more HRV parameters comprise one or more parameters selected from the group consisting of a high frequency (HF) index, a low frequency (LF) index, and an LF/HF ratio.

8. The method according to claim 1, characterized in that the step of analyzing the one or more HRV parameters and the respiratory signals using the predetermined drowsiness detection algorithm further comprises the steps of:
   determining, by the one or more processors, a threshold value of the LF/HF ratio based on one or more biometrical parameters of the driver;
   determining, by the one or more processors, a probability model and/or a threshold value of the respiratory signals based on one or more biometrical parameters of the driver; and
   storing, by one or more memory elements in a training module, the threshold value of the LF/HF and the probability model and/or the threshold value of the respiratory signals.

9. The method according to claim 1, characterized in that the predetermined drowsiness detection algorithm determines:
   an LF/HF ratio condition by comparing the LF/HF ratio with the probability model and/or the threshold value of the LF/HF ratio; and
   a respiratory condition by comparing the filtered respiratory signals with the probability model and/or the threshold value of the respiratory signals;
   whereby the drowsiness state of the driver is determined based on the LF/HF ratio condition and the respiratory condition.

10. The method according to claim 8, characterized in that the biometrical parameters of the driver comprise one or more parameters selected from the group consisting of an age, a gender, a body mass index (BMI), and a race group of the driver.

11. An in-vehicle monitoring and intervention system, comprising one or more processors and an apparatus, for determining a drowsiness state of a driver in a vehicle, characterized in that the apparatus comprises:

one or more ECG sensors;
one or more respiratory sensors; and
one or more filters selected from the group consisting of signal filters, adaptive filters, and FIR filters;

wherein:
the one or more processors are configured to execute a method of processing ECG signals, respiratory signals and acceleration signals for determining a drowsiness state of a driver according to the determination process of claim 1.

12. The in-vehicle monitoring and intervention system according to claim 11, characterized in that the apparatus further comprises one or more triaxial accelerometers; and an intervention module.

13. The in-vehicle monitoring and intervention system according to claim 12, characterized in that the intervention module further comprises a transmission module for sending an in-vehicle warning or a smartphone warning.

14. The in-vehicle monitoring and intervention system according to claim 11, characterized in that the one or more ECG sensors are being spaced from each other by a predetermined distance along the seat belt.

15. The in-vehicle monitoring and intervention system according to claim 11, characterized in that the one or more respiratory sensors are positioned on a seat belt for measuring the respiration pattern of the driver.

16. The in-vehicle monitoring and intervention system according to claim 11, characterized in that the apparatus further comprises a clip for attaching the apparatus to a seat belt of the vehicle as a discrete hardware apparatus.

17. The in-vehicle monitoring and intervention system according to claim 11, characterized in that the apparatus is integrated into a seat belt of the vehicle.

18. The in-vehicle monitoring and intervention system according to claim 11, characterized in that the one or more processors is connected to the one or more ECG sensors, the one or more respiratory sensors, and the one or more filters using wires, e-textiles, copper-nylon fabric, or other conductive textiles.

* * * * *